United States Patent [19]

Bujan et al.

[11] 4,451,255

[45] May 29, 1984

[54] DUAL FLOW RATE INTRAVENOUS ADMINISTRATION SET WITH SINGLE PUMP CHAMBER

[75] Inventors: Albert F. Bujan, Waukegan; Jack L. Harms, Mundelein, both of Ill.

[73] Assignee: Abbott Laboratories, North Chicago, Ill.

[21] Appl. No.: 379,823

[22] Filed: May 20, 1982

[51] Int. Cl.$^3$ .............................................. A61M 5/00
[52] U.S. Cl. .................................... 604/157; 604/81; 604/153
[58] Field of Search ................................. 604/80–86, 604/123, 151–153, 246, 251

[56] References Cited

U.S. PATENT DOCUMENTS

| | | | |
|---|---|---|---|
| 3,868,973 | 3/1975 | Bierman | 138/43 |
| 4,105,029 | 8/1978 | Virag | 604/81 |
| 4,200,095 | 4/1980 | Reti | 604/81 |
| 4,265,240 | 5/1981 | Jenkins | 604/81 |
| 4,336,800 | 6/1982 | Pastrone | 604/123 |

FOREIGN PATENT DOCUMENTS 2059776 4/1981 United Kingdom ................ 604/81

Primary Examiner—Dalton L. Truluck
Attorney, Agent, or Firm—Neil E. Hamilton

[57] ABSTRACT

A disposable intravenous administration set for use with a single pump chamber wherein a primary and secondary set are combined into a single I.V. pump set. The dual capacity set would be utilized in conjunction with an I.V. pump having a capacity for at least two distinct flow rates. The primary and secondary portions of the set are interconnected through a Y-type backcheck valve in the usual manner with the secondary source of liquid placed at a higher level than that of the primary. With the secondary set connected to a secondary source of liquid the pump will be set at a flow rate faster than that for the primary set. After the secondary source of liquid is depleted, the primary source will then be administered as the pump will automatically convert to the slower flow rate. In order to prevent the action of the pump from drawing any of the primary liquid into that of the secondary during administration of the secondary liquid, a restrictor is placed downstream of the backcheck valve or alternatively a drip chamber is utilized for the same purpose.

11 Claims, 7 Drawing Figures

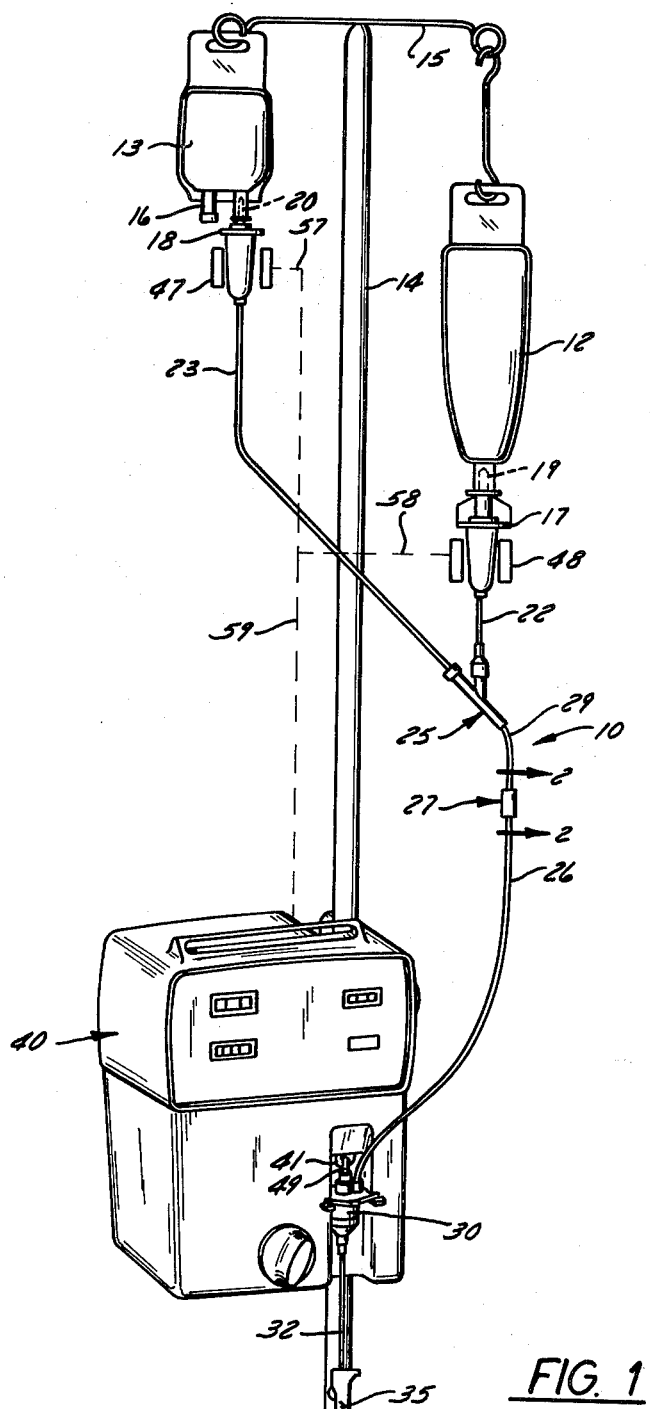
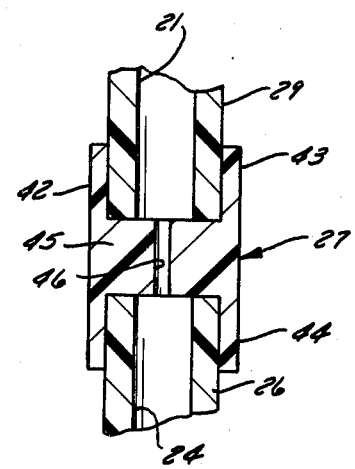
FIG. 1
FIG. 2

DUAL FLOW RATE INTRAVENOUS ADMINISTRATION SET WITH SINGLE PUMP CHAMBER

BACKGROUND OF THE INVENTION

This invention relates to an administration set which will prevent the administration of two different liquids at different flow rates through the same pump chamber. More particularly, this invention relates to an I.V. administration set having independent, dual flow rates yet utilizing a single pump chamber wherein the flow rates are effected with different fluids without the faster flow rate affecting the slower one or an intermixing of one liquid with the other. The prior art teaches the use of a primary set with an I.V. pump while controlling different flow rates therein. This is shown in U.S. Pat. Nos. 4,105,028 and 4,121,584. The control of separate fluids in an independent manner in an I.V. delivery system is described in U.S. Pat. No. 4,094,318. Nowhere in the prior art is there described the utilization of a single pumping chamber interconnected with a primary and secondary fluid administration set which can deliver one fluid at a given rate and another fluid at a slower rate without the flow rate of one affecting or intermixing liquid with the other.

It is an advantage of the present invention to provide a novel dual flow rate pump set which utilizes a single pump chamber. Other advantages are a dual flow rate I.V. set which employs only a single I.V. pump yet will obviate any mixing of the two liquids at the different flow rates; a dual flow rate I.V. set which is disposable and inexpensive to manufacture; and a dual flow rate I.V. set with a single pumping chamber wherein the chamber can be of various types of construction and activated by a wide variety of I.V. pumping devices currently in the marketplace.

SUMMARY OF THE INVENTION

The foregoing advantages are accomplished and the shortcomings of the prior art are overcome by the present dual flow rate I.V. pump set for pumping liquid from at least two separate sources by means of a single pumping device. The I.V. set of this invention includes a pump chamber having inlet and outlet ports in communication with a cavity portion with means to vary the volume of the cavity to effect the flow of liquid from the inlet port and out the outlet port. First and second lengths of flexible I.V. tubing are in fluid-tight communication with the inlet and outlet ports, respectively. Adapter means are provided to attach an intravenous needle to the second length of tubing opposite the chamber. Third and fourth lengths of flexible I.V. tubing have container connection means associated therewith. Valve means including a valve body with interconnected fluid passage means communicate with the first, third and fourth lengths of flexible tubing. The valve body includes liquid flow control means to selectively control the flow of liquid in one of the third or fourth lengths of tubing in response to liquid flow in the other. Means are operatively associated with the first length of tubing and positioned between the valve means and the pump chamber to restrict or interrupt fluid flow in the first length of tubing. In a preferred manner, the means to restrict or interrupt fluid flow in the first length of tubing is defined by means to effect a pressure differential therein. In one manner, the means to effect the pressure differential is afforded by a flow restrictor in the form of a restrictive or smaller passageway than that provided by the tubing. In another manner the pressure differential is afforded by means to interrupt the flow such as by the use of a common drip chamber. As the I.V. pump will effect a pumping action in the pump chamber cavity the pressure differential means will prevent the slight vacuum formed at the inlet side of the pump chamber from effecting any pressure drop in the backcheck valve whereby an undesired opening of the valve to the primary I.V. set would otherwise be caused. dr

BRIEF DESCRIPTION OF THE DRAWINGS

A better understanding of the dual flow rate I.V. pump set will be accomplished by reference to the drawings wherein:

FIG. 1 is a view in side elevation of a dual flow rate I.V. pump set using a single chamber positioned in conjunction with an I.V. pump which is shown in a perspective view.

FIG. 2 is an enlarged view in vertical section of a flow restrictor utilized in the I.V. set illustrated in FIG. 1 and taken along line 2—2 thereof.

DESCRIPTION OF ONE EMBODIMENT

Figure 3:
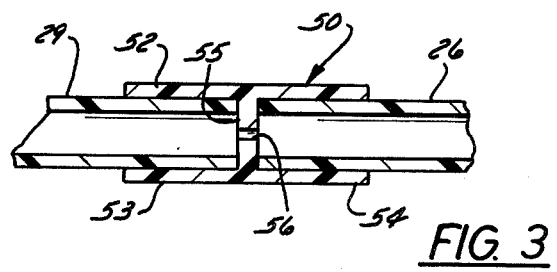
FIGS. 3, 4, 5 and 6 are views in vertical section illustrating various other types of flow restrictors used in connection with the dual flow rate I.V. set shown in FIG. 1.

Proceeding to a detailed description of one embodiment of the present invention, the dual flow rate I.V. pump administration set 10 is illustrated in FIG. 1 and will be utilized in conjunction with an I.V. pump shown generally at 40. The I.V. pump set is shown interconnected to the usual flexible I.V. containers 12 and 13 suitably supported from a support post 14 from which extends support arm 15. Two drip chambers 17 and 18 are in fluid communication with containers 12 and 13, respectively, by means of piercing pins 19 and 20, respectively. Extending from the respective drip chambers are lengths of tubing 22 and 23 which are connected in a fluid-tight manner with backcheck valve mechanism 25. Extending from the opposing end of the backcheck valve 25 is an additional length of tubing 29 secured to a flow restrictor generally 27. Another length of tubing 26 interconnects restrictor 27 with pump chamber 30. Extending from the lower end of pump chamber 30 are additional lengths of tubing 32, 33 and 34 which are interconnected by means of Y reseal devices 36 and 37. A flow control clamp 35 is attached to tubing 32. A needle adapter 38 is secured to tubing 34 and has hypodermic needle 39 attached thereto. The usual drop detectors 48 and 47 are operatively positioned with respect to drip chambers 17 and 18 with conductor lines 58, 57 and 59 making the usual electrical connection with pump 40.

As best seen in FIG. 2, flow restrictor 27 interconnects lengths of tubing 29 and 26 by means of a cylindrical body section 42 with extensions 43 and 44 providing compartments for fluid-tight engagement with the tubing lengths when they are abutted against intermediate section 45. A restrictive passageway 46 extends through intermediate section 45 to provide a fluid passage of smaller cross section between tubing 29 and 26. A somewhat similar flow restrictor is illustrated in FIG. 3 and is designated generally by the numeral 50. It is similar to that illustrated at 27 in having a substantially H-shaped and cylindrical body section 52 with extensions 53 and 54. The major difference is that the intermediate section 55 is smaller in width than 45 with passageway 56 therein. Extensions 53 and 54 will afford fluid-tight connection for tubing 29 and 26 with the inside dimension of the extensions being substantially the same as the outside diameter of the tubing.

Figure 4:
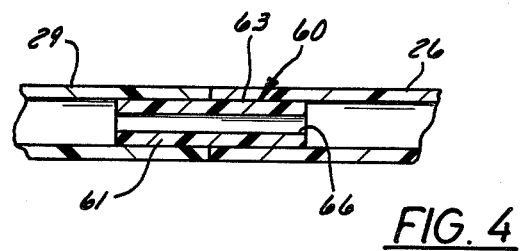

Another type of flow restrictor generally 60 is shown in FIG. 4 wherein a cannula 61 or smaller length of tubing, which is preferably rigid or semirigid, is placed inside tubing lengths 29 and 26. In this instance the outer surface 63 of cannula 61 will have approximately the same outside diameter as the inside diameter of tubing 29 and 26. In this manner tubing lengths 26 and 29 will be secured thereto in a fluid-tight manner as well as being abutted against each other.

Figure 5:
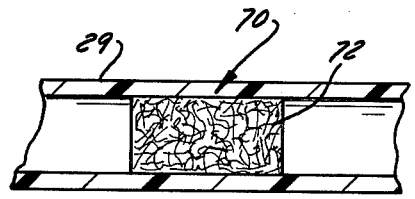
Figure 6:
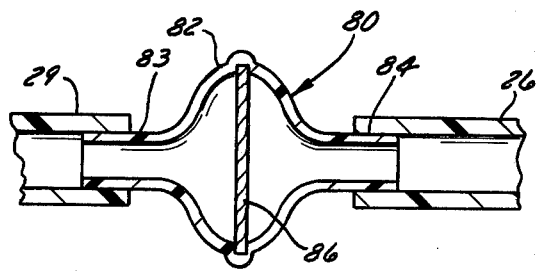

A further modified form of a flow restrictor 70 is illustrated in FIG. 5 wherein a porous plug in the form of cylinders is positioned inside tubing 29. The porous plug is referred to by 72 and, as is true of cannula 61, will have an outside diameter substantially the same as the inside diameter of tubing 29. In FIG. 6, a further flow restrictor, generally 80 is shown in conjunction with tubing lengths 29 and 26. This restrictor has a tubular-like body section 82 with extensions 83 and 84 for connection with the respective length of tubing. Disposed therebetween is an enlarged diameter portion with a filter membrane 86 of the hydrophilic type. The filter membrane is secured in body section 82 through a circumferential bead of plastic.

DESCRIPTION OF AN ALTERNATIVE EMBODIMENT

Figure 7:
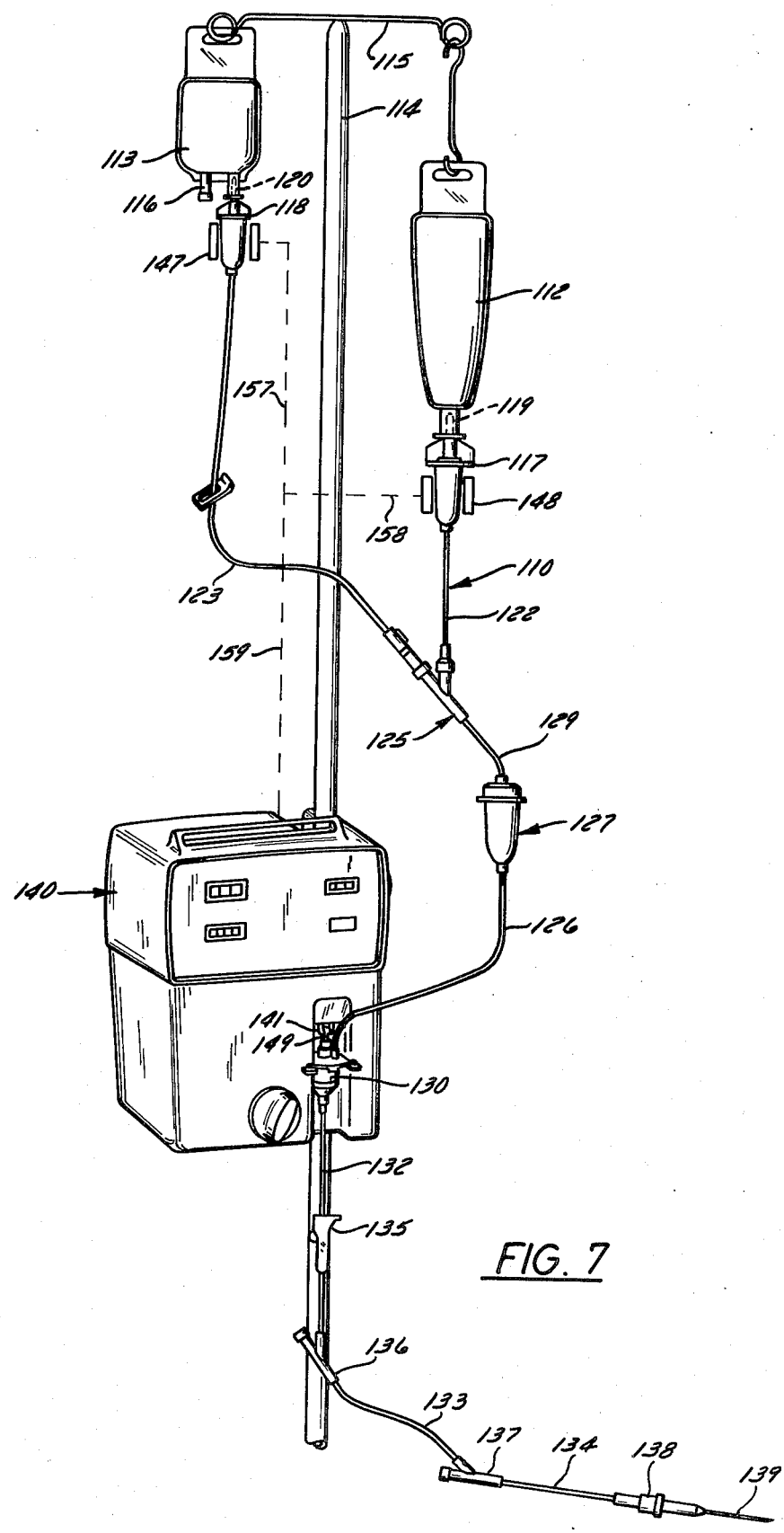
FIG. 7 is a view similar to that of FIG. 1 except showing an alternative embodiment.

In FIG. 7 there is described an alternative embodiment generally 110. Similar parts are numbered with similar numbers with respect to embodiment 10 except that they are designated in the "100" series. Those parts which are the same will not be again described in detail as they are obvious from the numerical designation. The major difference between embodiment 10 and 110 is in the type of flow interruption means 127. In this instance flow interruption means 127 is in the form of a standard drip chamber interconnecting tubing 129 and 126, rather than a means to restrict flow such as flow restrictor 27.

OPERATION

A better understanding of the advantages of the dual flow rate pump administration sets 10 and 110 will be had by a description of their operation. Referring to unit 10 first, it will be packaged separately from containers 12 and 13 under the usual sterile packaging conditions. When it is desired to utilize set 10, pump chamber 30 will be suitably positioned in pump 40 and piercing pins 19 and 20 will be placed in fluid-tight communication with containers 12 and 13 in the usual manner. As this set is specifically adapted to be utilized as a secondary I.V. administration set or what is commonly known in the industry as a "piggyback," container 13 will be of an additive type wherein the solution will be delivered at a faster rate than that of the primary container 12. For this purpose container 13 will be provided with an additive port 16 whereby an additional medicinal material can be added through the port 16 or alternatively a medicinal product such as an antibiotic can be packaged in the container and a sterile solution such as an electrolyte solution can be added through the additive port 16.

It will be understood that I.V. pump 40 will be of a dual capacity type such as that currently marketed by Abbott Laboratories of North Chicago, Ill. under the trade name Abbott/Shaw Lifecare Volumetric Pump, Model 3. I.V. fluid container 12 will contain the usual I.V. solution such as 5% saline and will be supported from post 15 as will container 13. With the administration set 10 positioned in a manner indicated in FIG. 1 in conjunction with I.V. pump 40, the set 10 will be primed in the usual manner. The controls of pump 40 will be set in a manner to deliver two different flow rates through the activation of driver mechanism 41 and driver 49. A faster rate will be programmed for delivery of the secondary solution and container 13 and a slower one for the primary solution in container 12. As container 13 is placed at a higher level than container 12, the pressure of the fluid will flow through tubing 23 and into backcheck valve mechanism 25 to thereby close the valve and flow to tubing 22. For example if one were to give 100 ml. of a broad-spectrum antimicrobial such as Keflin from container 13 at 200 ml. per hour, the I.V. pump set would be so programmed and would be programmed later to deliver the solution from container 12 at a flow rate of 50 ml. per hour. In this instance, the pump 40 with the dual flow rate set 10 would operate as follows: pump 40 would be programmed to deliver at 200 ml. per hour for 30 minutes and then automatically change to 50 ml. for whatever time desired at that rate. The secondary container 13 would empty in 30 minutes and the backcheck mechanism 25 would release and allow the primary container 12 to start to deliver while the pump reverted to the 50 ml. per hour rate. The dual flow rate drop detectors 47 and 48 would monitor the respective flow rates to be certain that the proper rate is achieved.

During the previously described procedure it will be recognized that as driver mechanism 41 pushes downwardly and pulls upwardly on driver 49 of pump chamber 30 a reduction of pressure will be effected at the inlet side and in tubing 26. If it were not for some means to effect a pressure differential or interrupt fluid flow before this reduction in pressure is transmitted to the backcheck mechanism 25, the reduced pressure could open the backcheck valve and cause an undesired flow from container 12 while flow was being effected from container 13. In this instance, this is prevented by flow restrictor 27. With reference to FIG. 2 it will be seen that a relatively narrow passageway 46 is provided between the passageways 21 and 24 of tubing 26 and 29. It is this narrow restriction which will prevent the reduction in pressure being transmitted to the backcheck valve mechanism 25. With respect to FIG. 3, the same effect will be accomplished with passage 56 as well as with passageway 66 in flow restrictor 60. In FIG. 5, the porous plug 72 will serve as a flow restrictor and in a similar manner the filter membrane 86 in restrictor 80 shown in FIG. 6. In each instance, the reduction of pressure should be such that pulsitol flow is minimized.

Dual flow rate set 110 will operate in substantially the same manner as that previously described for unit 10. The major difference in the utilization of the flow interrupter 127 is in the form of a drip chamber. It will be appreciated that as pump unit 140 exerts a driving force on pump chamber 30 any reduction in pressure in line 126 will be relieved by means of the interval volume of chamber 127 and will not be transmitted to the backcheck mechanism 125. Accordingly, backcheck valve mechanism will remain closed to line 122 when secondary fluid is flowing through line 123 through tubing 129 and 126 to the pump chamber 130.

The body portions 42 and 52 of flow restrictors 27 and 50 can be easily fabricated from a thermoplastic material with the passageways 46 and 56 being molded therein. In the instance of flow restrictor cannula 61, it is made from extruded plastic material. Preferably it will have an outside diameter of 0.138 inch and an inside diameter of 0.030 inch. Porous plug 72 is preferably fabricated from a open cell foamed material. However, other porous-type materials such as sintered metal or plastic could be utilized. Filter membrane 86 can be of the cast polymer type. Alternatively filter materials composed of woven or nonwoven type could be employed. In the instance of porous plug 72 and filter member 86, the important aspect is that they provide a pressure resistance and be hydrophilic.

It will thus be seen that through the present invention there is provided a dual flow rate I.V. administration set which obviates the use of two separate pumping chambers and consequently two I.V. pumps or controllers. The I.V. set of this invention can be easily fabricated without substantial added cost to the standard I.V. set. It can be utilized in conjunction with standard I.V. solution containers, standard I.V. pumps and drop detection equipment without the need for special instruction.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

What is claimed is:

1. An intravenous administration set for pumping liquid from at least two separate source by means of a single pumping device comprising:
   a pump chamber having inlet and outlet ports in communication with a cavity portion with means to vary the volume of said cavity to effect a flow of liquid from said inlet port and out said outlet port;
   first and second lengths of flexible I.V. tubing in fluid-tight communication with said inlet and outlet ports, respectively;
   means to attach an intravenous needle connected to said second length of tubing opposite said chamber;
   third and fourth lengths of flexible I.V. tubing;
   container connection means operatively associated with said third and fourth lengths of flexible tubing;
   backcheck valve means including a valve body with interconnected fluid passage means for fluid-tight communication with said first, third and fourth lengths of flexible tubing, said valve body including liquid flow control means to selectively control the flow of liquid in said one of said third and fourth lengths of tubing in response to liquid flow in the other; and
   flow restriction or interruption means defined by a body section with a flow passage operatively connected to said first length of tubing and positioned between said backcheck valve means and pump chamber to restrict or interrupt fluid flow therein, so that when the volume of said pump chamber cavity is reduced by a pumping device, any reduction in pressure will not be transmitted through said first length of tubing to said backcheck valve means.

2. The intravenous administration set for pumping liquid from at least two separate sources by means of a single pumping device as defined in claim 1 wherein said means to restrict or interrupt fluid flow is defined by means to effect a reduction in pressure in said first length of tubing.

3. The intravenous administration set for pumping liquid from at least two separate sources by means of a single pumping device as defined in claim 2 wherein said means to effect a reduction in pressure is defined by a passageway having a channel with a cross section smaller than that of said first tubing.

4. The intravenous administration set for pumping liquid from at least two separate sources by means of a single pumping device as defined in claim 3 wherein said passageway is provided by a length of tubing having an outside diameter of substantially the same size as the inside diameter of said first length of tubing.

5. The intravenous administration set for pumping liquid from at least two separate sources by means of a single pumping device as defined in claim 3 wherein said passageway is provided by a combined tubing connector and restrictor means defined by a substantially H-shaped body in cross section with the inside dimension of the extensions of said body portion being substantially the same as the outside diameter of said first length of tubing.

6. The intravenous administration set for pumping liquid from at least two separate sources by means of a single pumping device as defined in claim 2 wherein said means to effect a reduction in pressure is defined by a porous plug member having an outside diameter substantially the same as the inside diameter of said first length of tubing.

7. The intravenous administration set for pumping liquid from at least two separate sources by means of a single pumping device as defined in claim 2 wherein said means to effect a reduction in pressure is defined by a filter membrane positioned in fluid flow contact with said first length of tubing.

8. The intravenous administration set for pumping liquid from at least two separate sources by means of a single pumping device as defined in claim 7 wherein said filter membrane is supported by a tubular body member with the opposing ends of said body member in fluid-tight communication with said first length of tubing.

9. The intravenous administration set for pumping liquid from at least two separate sources by means of a single pumping device as defined in claim 1 wherein said means to interrupt fluid flow is defined by a standard drip chamber.

10. The intravenous administration set for pumping liquid from at least two separate sources by means of a single pumping device as defined in claim 1 wherein said pump chamber includes a driver element adapted to be engaged by a driver mechanism.

11. The intravenous administration set for pumping liquid from at least two separate sources by means of a single pumping device as defined in claim 1 wherein said container connection means includes a standard drip chamber.

* * * * *